(12) United States Patent
Nun

(10) Patent No.: US 6,623,479 B1
(45) Date of Patent: Sep. 23, 2003

(54) CRYOSURGICAL INSTRUMENT

(75) Inventor: Yehoshua Ben Nun, Vitkin (IL)

(73) Assignee: Aggart Invest Inc., Tortola (VG)

( * ) Notice: Subject to any disclaimer, the term of this patent is extended or adjusted under 35 U.S.C. 154(b) by 0 days.

(21) Appl. No.: 09/786,858

(22) PCT Filed: Sep. 9, 1999

(86) PCT No.: PCT/IL99/00491

§ 371 (c)(1),
(2), (4) Date: Aug. 22, 2001

(87) PCT Pub. No.: WO00/15129

PCT Pub. Date: Mar. 23, 2000

(30) Foreign Application Priority Data

Sep. 11, 1998  (IL) ................................................. 126182

(51) Int. Cl.⁷ .............................................. A61B 18/18
(52) U.S. Cl. .............................. 606/21; 606/22; 606/23
(58) Field of Search ..................................... 606/20–24

(56) References Cited

U.S. PATENT DOCUMENTS

| | | |
|---|---|---|
| 3,536,075 A | 10/1970 | Thomas et al. |
| 3,942,519 A | 3/1976 | Shock |
| 3,976,077 A | 8/1976 | Kerfoot, Jr. |
| 5,108,390 A | 4/1992 | Potocky et al. |
| 5,139,496 A | 8/1992 | Hed |
| 5,207,674 A | 5/1993 | Hamilton |
| 5,654,546 A | 8/1997 | Lindsay |
| 5,674,218 A | 10/1997 | Rubinsky et al. |
| 5,733,280 A | 3/1998 | Avitall |
| 6,306,161 B1 * | 10/2001 | Ginsburg .................... 607/106 |

FOREIGN PATENT DOCUMENTS

| | | |
|---|---|---|
| GB | 2 226 497 A | 7/1990 |
| WO | WO 92/20289 A1 | 11/1992 |
| WO | WO 98/19595 A1 | 5/1998 |

* cited by examiner

*Primary Examiner*—Rosiland S. Kearney
(74) *Attorney, Agent, or Firm*—Browdy and Neimark, P.L.L.C.

(57) ABSTRACT

A cryosurgical instrument including a long, resiliently flexible cable terminating at a freezing unit with a selectively operable thermoelectric cooling device for normally freezing a leading contact tip.

10 Claims, 3 Drawing Sheets

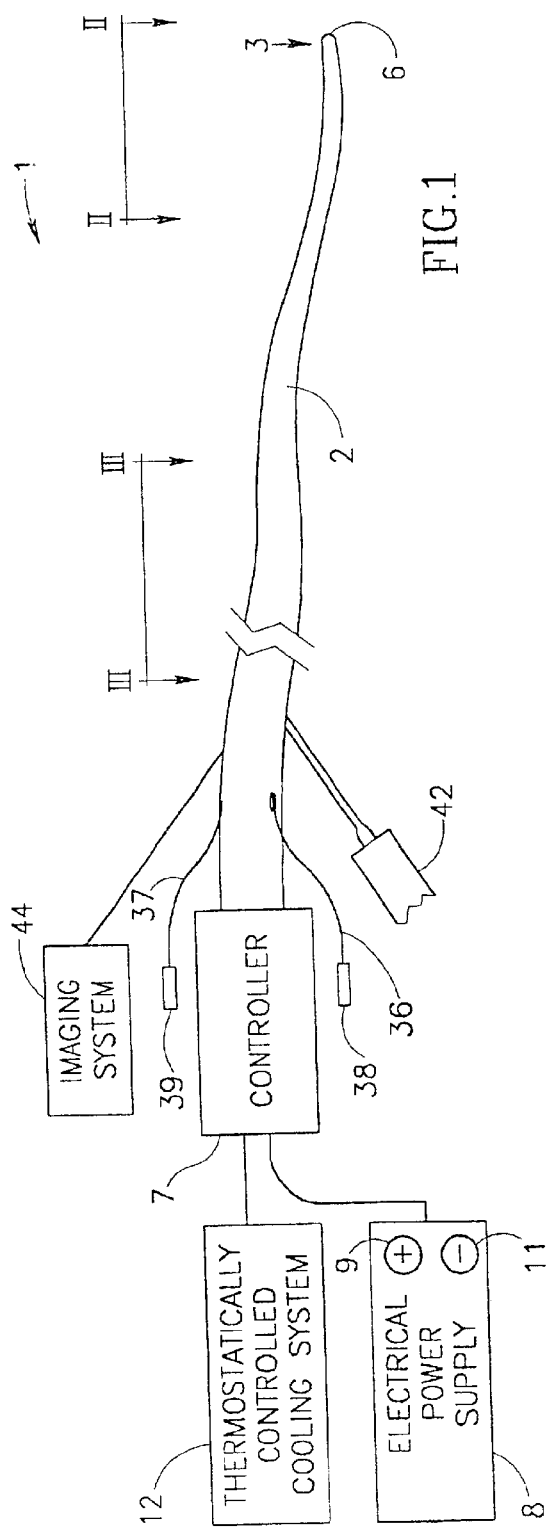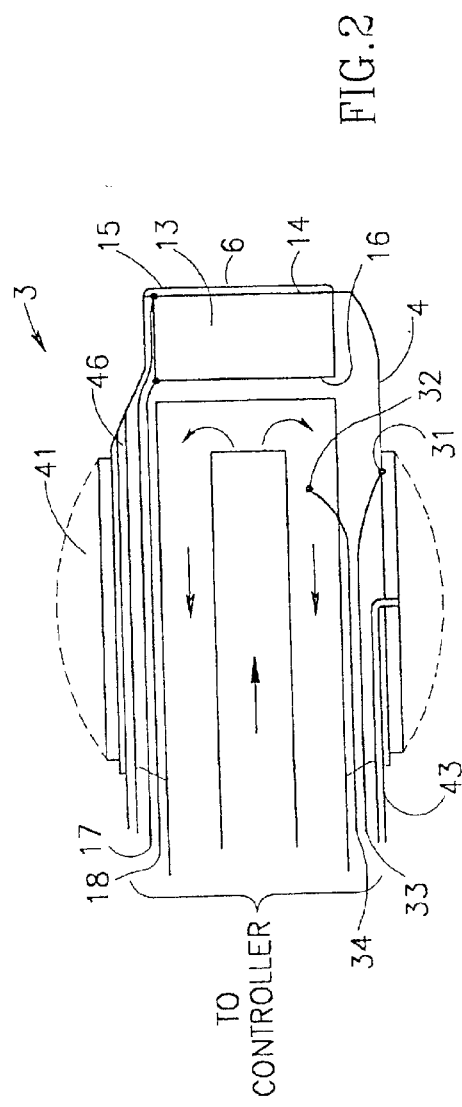

CRYOSURGICAL INSTRUMENT

FIELD OF THE INVENTION

The invention relates to a cryosurgical instrument for cryosurgical procedures in body lumens.

BACKGROUND OF THE INVENTION

The conventional surgical technique for removing a foreign object aspirated into a patient's lungs is by means of the introduction of a flexible bronchoscope with a conduit enabling the insertion of fine forceps for retrieval of the object. However, such a foreign object can be smooth or flat and therefore difficult to grip thereby precluding its removal by forceps and necessitating a more invasive surgical technique.

SUMMARY OF THE INVENTION

In accordance with the present invention, there is provided a cryosurgical instrument comprising a long, resiliently flexible cable terminating at a freezing unit with a selectively operable thermoelectric cooling device for normally freezing a leading contact tip.

By virtue of the design of the cryosurgical instrument of the present invention, cryosurgery is now facilitated in body lumens which hitherto have been inaccessible to conventional direct access cryosurgical instruments having rigid probes, for example, as illustrated and described in U.S. Pat. No. 3,942,519 to Shock. The cryosurgical instrument of the present invention affords a wide range of newly envisaged cryosurgical procedures in body lumens of both human and animal subjects accessible via either physiological openings or minimally invasive surgical openings. Such procedures include those hitherto performed by conventional surgical procedures for example, removing a foreign body from a patient's lung, and also inter alia cryoablation of tumors, removing naturally occurring stones such as gallbladder stones, kidney stones from the urinary tract, obstructing foreign bodies from the bowels, and the like.

BRIEF DESCRIPTION OF THE DRAWINGS

In order to understand the invention and to see how it may be carried out in practice, a preferred embodiment will now be described, by way of a non-limiting example only, with reference to the accompanying drawings, in which:

FIG. 1 is a pictorial view of a cryogenic instrument of the present invention having a long, resiliently flexible cable terminating at a freezing unit with a leading contact tip;

FIG. 2 is a longitudinal cross sectional close-up view of the freezing unit along line II—II in FIG. 1;

DETAILED DESCRIPTION OF THE DRAWINGS

Figure 3:
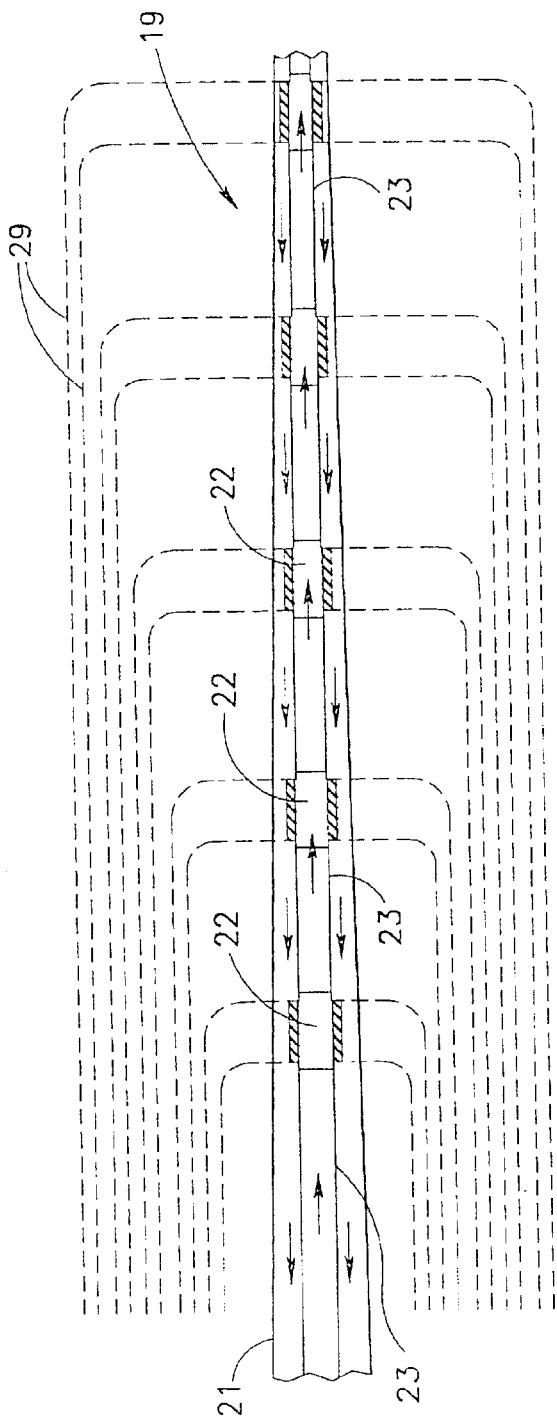
FIG. 3 is a longitudinal cross sectional view of the cable along line III—III in FIG. 1.
Figure 4:
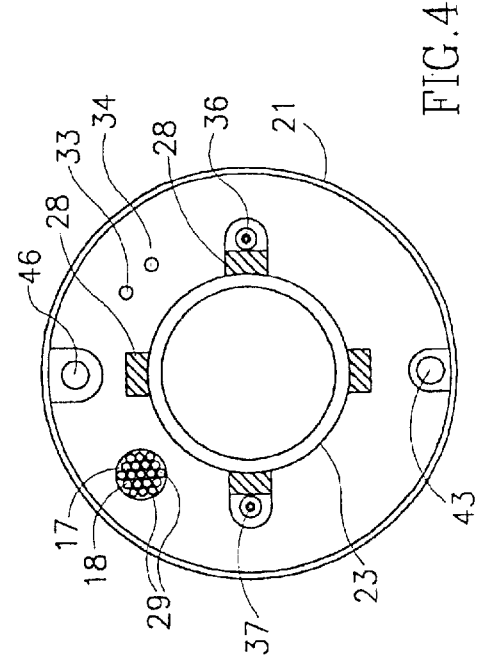
FIG. 4 is a transverse cross sectional view of the cable along line IV—IV in FIG. 1.
Figure 5:
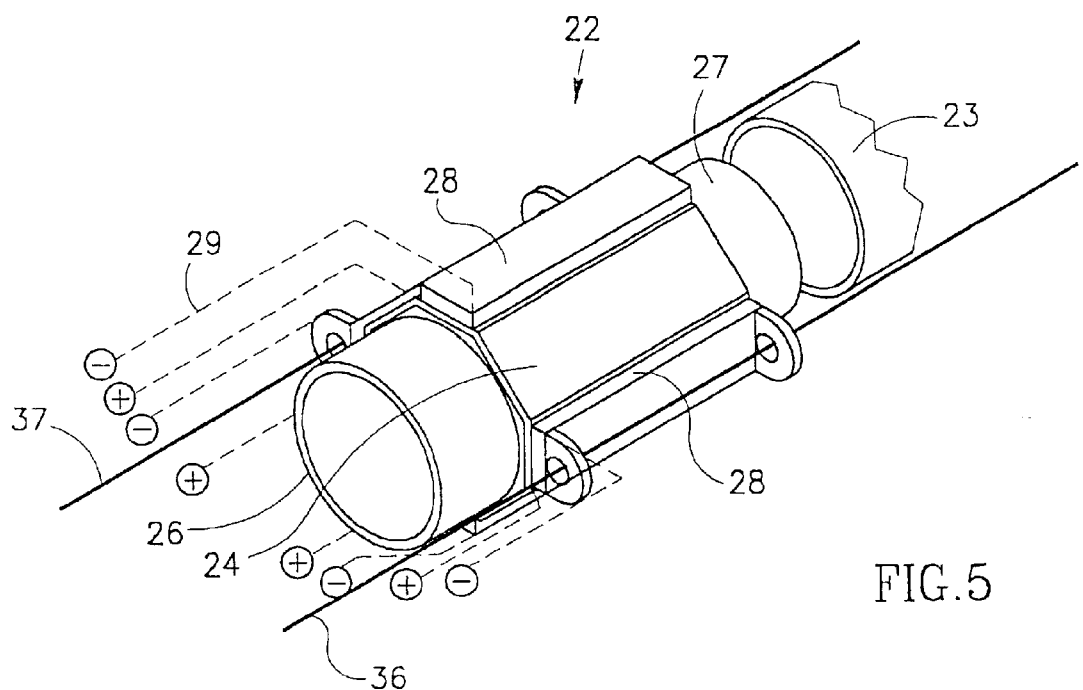
FIG. 5 is a perspective view of a cooling unit for chilling an upstream flow of cooling fluid.

With reference now to FIGS. 1 to 5, a cryogenic instrument 1 includes a long, resiliently flexible cable 2 terminating at a freezing unit 3 with a trailing external casing surface 4 and a leading contact tip 6. The contact tip 6 has a typical freezing temperature of between about −40° C. and about −70° C. whilst the casing surface 4 has a preferred temperature of about 25° C. The cryosurgical instrument 1 includes a controller 7 connected to an electrical power supply 8 with positive and negative terminals 9 and 11, and a thermostatically controlled cooling system 12.

The freezing unit 3 has a thermoelectric cooling device (hereinafter TEC device) 13 with a distal surface 14 and a proximal surface 16. The distal surface 14 is covered by a polymeric or similar protective covering 15 acting as the leading contact tip 6, and thereby precluding direct contact with the TEC device 13. The distal and proximal surfaces 14 and 16 are selectively and reversibly connected to the power supply's terminals 9 and 11 by lengthwise extending electrical wires 17 and 18 whereby the cryogenic instrument 1 has three operative states: a stand-by inoperative state in which the TEC device 13 is disconnected from the power supply 8; a first operative state for normally freezing the contact tip 6 by connecting the TEC device's distal and proximal surfaces 14 and 16 to the power supply's positive and negative terminals 9 and 11, respectively; and a second operative state for occasionally heating the contact tip 6, for example, to release a frozen surgical tissue, if necessary, by connecting the TEC device's distal and proximal surfaces 14 and 16 to the power supply's negative and positive terminals 11 and 9, respectively.

The cooling system 12 includes an inlet tube 19 centrally disposed in an outlet tube 21 for delivering an upstream flow of cooling fluid, for example, water via for cooling the freezing unit 3 and in particular the TEC device's normally hot proximal surface 16. The inlet tube 19 includes cooling units 22 interdisposed between tube segments 23, each cooling unit 22 having a hollow housing 24 with an inlet port 26 and an outlet port 27. Each cooling unit 22 is integrally formed with four TEC devices 28 circumferentially disposed thereabout and connected to the power supply 8 by lengthwise extending electrical wires 29 (schematically shown in FIG. 3 as being exterior to the cable 2) for chilling the upstream flow of cooling fluid such that it arrives at the freezing unit 3 at near zero Celsius temperature, thereby minimizing the flow rate of cooling fluid required for cooling purposes. The cooling units 22 are progressively smaller in size in an upstream direction and are designed for the step wise reduction of the cross sectional area of adjacent tube segments 23 in an upstream direction for lowering the required pressure differential along the inlet tube 19 whilst ensuring a sufficient flow of cooling fluid. The controller 7 receives temperature feedback for controlling the cooling system 12 and TEC devices 28 from a temperature sensor 31 sensing the temperature of freezing unit's external casing surface 4 and a temperature sensor 32 disposed adjacent to the inlet tube's outlet port, the sensors 31 and 32 being connected to the controller 7 by lengthwise extending electrical wires 33 and 34, respectively (see FIG. 2).

The cryogenic instrument 1 is provided with a pair of diametrically opposite guide wires 36 and 37 extending in a downstream direction from the TEC device 13, passing through guide loops 38 provided on the cooling units 22 and terminating in handles 38 and 39, respectively, for manipulating the freezing unit 3 to a desired location in a body lumen and/or cavity.

The freezing unit 2 is encircled by an inflatable sleeve 41 for selectively distending a narrow body lumen, the sleeve 41 being in flow communication with a pressure source, for example, a manually operated syringe 42, via a lengthwise extending tube 43.

The cryogenic instrument 1 is preferably employed with an imaging system 44 connected to a lengthwise extending fiber optic 46 providing a forward looking field of view.

Figure 6:
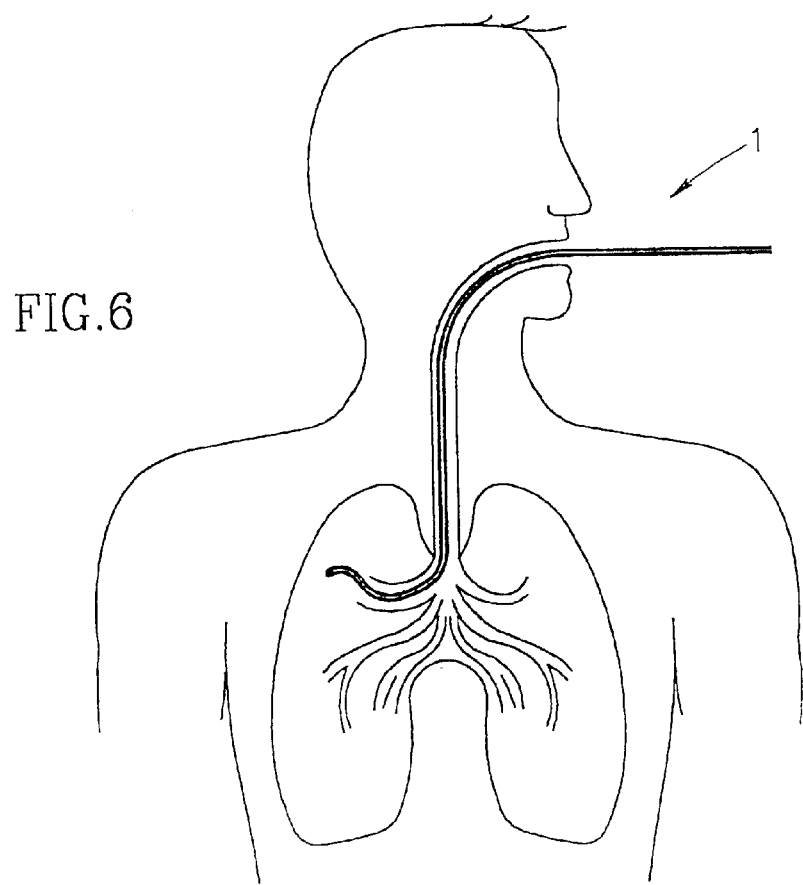
FIG. 6 is a pictorial view showing the use of the cryogenic instrument of the present invention for removing a foreign object from a human subject's lung.

In FIG. 6, a surgeon introduces the cryogenic instrument 1 into a patient's lung at a target site at which a foreign body has been identified. The surgeon operates the cryogenic instrument 1 to freeze the contact tip 6 whereupon its contact with the foreign body freeze grips the foreign body thereto enabling its removal from the patient's lung.

While the invention has been described with respect to a limited number of embodiments, it will be appreciated that many variations, modifications and other applications of the invention can be made by those ordinarily skilled in the art without departing from the scope of the claims appended hereto.

What is claimed is:

1. A cryosurgical instrument comprising a long, resiliently flexible cable terminating at a freezing unit associated with a leading contact tip, said freezing unit incorporating a selectively operable thermoelectric cooling device for normally freezing said leading contact tip, said cooling device having a distal surface acting as said leading contact tip of the freezing unit, and a proximal surface at which the cooling device terminates, the instrument further comprising an inlet tube extending along said resiliently flexible cable and terminating adjacent said proximal surface of the cooling device, for delivering an upstream flow of cooling fluid from an external cooling system to said proximal surface, said inlet tube being provided with at least one cooling unit extending along a portion of the inlet tube's length and spaced from said proxumal surface of the cooling device, for chilling said upstream flow of cooling fluid before it arrives to said proximal surface.

2. A cryosurgical instrument according to claim 1, wherein the thermoelectric cooling device of said freezing unit is capable of keeping said contact tip at a freezing temperature of between about −40° C. and about −70° C., whilst said at least one cooling unit is adapted for chilling the upstream flow of cooling fluid such that it arrives at the freezing unit at near 0° C. temperature.

3. A cryosurgical instrument according to claim 1, comprising a plurality of the cooling units inter-disposed between segments of said inlet tube.

4. A cryosurgical instrument according to claim 3, wherein each cooling unit includes at least one thermoelectric cooling device.

5. A cryosurgical instrument according to claim 1, wherein said inlet tube tapers towards said freezing unit.

6. A cryosurgical instrument according to claim 1, wherein said cooling device is capable of selectively heating said contact tip.

7. A cryosurgical instrument according to claim 1, further comprising an inflatable sleeve adjacent said freezing unit for selectively distending a narrow body lumen.

8. A cryosurgical instrument according to claim 1, wherein said inlet tube together with at least said one cooling unit is disposed within an outlet tube for delivering said cooling fluid away from said freezing unit towards said external cooling system.

9. A cryosurgical instrument according to claim 1, wherein each cooling unit comprises a hollow housing for the passage of cooling fluid therethrough and a plurality of thermoelectric cooling devices circumferentially disposed thereabout.

10. A cryosurgical instrument according to claim 9, further comprises a pair of diametrically opposite guiding means extending in a downstream direction from said freezing unit and passing through said plurality of cooling units for manipulating the freezing unit.

* * * * *